(12) United States Patent
Menci et al.

(10) Patent No.: US 10,117,687 B2
(45) Date of Patent: Nov. 6, 2018

(54) INTRAMEDULLARY NAIL FOR THE TREATMENT OF FRACTURES OF THE LONG BONES

(71) Applicants: Pier Giovanni Menci, Anagni (IT); Romano Menci, Anagni (IT); Mauro Di Tomassi, Frosinone (IT); Pier Luigi Caprioli, Rome (IT)

(72) Inventors: Pier Giovanni Menci, Anagni (IT); Romano Menci, Anagni (IT); Mauro Di Tomassi, Frosinone (IT); Pier Luigi Caprioli, Rome (IT)

( * ) Notice: Subject to any disclaimer, the term of this patent is extended or adjusted under 35 U.S.C. 154(b) by 0 days.

(21) Appl. No.: 15/560,747

(22) PCT Filed: Mar. 24, 2016

(86) PCT No.: PCT/IT2016/000074
§ 371 (c)(1),
(2) Date: Sep. 22, 2017

(87) PCT Pub. No.: WO2016/151611
PCT Pub. Date: Sep. 29, 2016

(65) Prior Publication Data
US 2018/0250040 A1  Sep. 6, 2018

(30) Foreign Application Priority Data
Mar. 25, 2015 (IT) .............................. FR2015A0005

(51) Int. Cl.
*A61B 17/72* (2006.01)
*A61B 17/74* (2006.01)
*A61B 17/86* (2006.01)

(52) U.S. Cl.
CPC .......... *A61B 17/725* (2013.01); *A61B 17/744* (2013.01); *A61B 17/7283* (2013.01); *A61B 17/8625* (2013.01)

(58) Field of Classification Search
CPC ...................................... A61B 17/72–17/7291
See application file for complete search history.

(56) References Cited

U.S. PATENT DOCUMENTS 3,025,853 A * 3/1962 Mason ................. A61B 17/746
411/478
3,216,414 A * 11/1965 Street .................. A61B 17/746
411/446

(Continued)

FOREIGN PATENT DOCUMENTS

DE   102007029090 A1    12/2008
DE   102009010328 A1 *   8/2010 ........... A61B 17/725

(Continued)

OTHER PUBLICATIONS

Search Report dated Aug. 19, 2015 of corresponding Italian application No. FR2015A000005; 8 pgs.

(Continued)

*Primary Examiner* — Eduardo C Robert
*Assistant Examiner* — Michelle C Eckman
(74) *Attorney, Agent, or Firm* — Maier & Maier, PLLC

(57) ABSTRACT

An intramedullary nail for the treatment of fractures of long bones. The nail presents a body having a proximal area and a distal area and a longitudinal axis, and is adapted to be inserted in the medullary canal of said long bone. Furthermore, the nail presents at least two through holes formed at the proximal zone of said body. The nail includes a pair of fastening elements each having a first and a second end, in which each fastening element is adapted to be housed in a respective hole of the body of the nail at the respective first end.

14 Claims, 11 Drawing Sheets

(56) References Cited

U.S. PATENT DOCUMENTS

| | | | | |
|---|---|---|---|---|
| 3,892,233 | A | * | 7/1975 | Vestby .................. A61B 17/74 606/67 |
| 4,103,683 | A | * | 8/1978 | Neufeld ............. A61B 17/1721 606/64 |
| 4,561,432 | A | * | 12/1985 | Mazor ................ A61B 17/1721 606/68 |
| 4,978,349 | A | * | 12/1990 | Frigg ................ A61B 17/1721 606/62 |
| 5,741,256 | A | * | 4/1998 | Bresina ................ A61B 17/744 606/62 |
| 6,019,761 | A | | 2/2000 | Gustilo |
| 6,270,499 | B1 | * | 8/2001 | Leu ........................ A61B 17/72 606/62 |
| 6,319,253 | B1 | * | 11/2001 | Ackeret ................ A61B 17/72 606/64 |
| 6,379,360 | B1 | * | 4/2002 | Ackeret ............. A61B 17/1725 606/60 |
| 6,409,730 | B1 | * | 6/2002 | Green ................... A61B 17/74 606/232 |
| 6,558,388 | B1 | * | 5/2003 | Bartsch ............. A61B 17/7225 606/62 |
| 6,648,889 | B2 | * | 11/2003 | Bramlet .............. A61B 17/725 606/310 |
| 7,744,638 | B2 | * | 6/2010 | Orbay ................ A61B 17/8047 606/280 |
| 7,780,710 | B2 | * | 8/2010 | Orbay ................ A61B 17/8061 606/286 |
| 8,449,544 | B2 | * | 5/2013 | Grusin ............... A61B 17/7225 606/64 |
| 2003/0083663 | A1 | * | 5/2003 | Goldhahn ............. A61B 17/68 606/291 |
| 2004/0049192 | A1 | * | 3/2004 | Shimizu ............. A61B 17/7098 606/62 |
| 2004/0068258 | A1 | * | 4/2004 | Schlapfer ............... A61B 17/70 606/261 |
| 2005/0010226 | A1 | * | 1/2005 | Grady, Jr. ............ A61B 17/746 606/281 |
| 2005/0055024 | A1 | * | 3/2005 | James .................. A61B 17/164 606/64 |
| 2005/0165395 | A1 | * | 7/2005 | Orbay ................ A61B 17/8061 606/60 |
| 2009/0192512 | A1 | * | 7/2009 | Sommers ............... A61B 17/68 606/64 |
| 2010/0094293 | A1 | * | 4/2010 | McClellan ......... A61B 17/7241 606/64 |
| 2013/0096629 | A1 | * | 4/2013 | Rollinghoff ............ A61B 17/80 606/281 |
| 2013/0317502 | A1 | * | 11/2013 | Overes .................. A61B 17/74 606/66 |
| 2014/0148859 | A1 | * | 5/2014 | Taylor ................ A61B 17/8061 606/282 |
| 2015/0134016 | A1 | * | 5/2015 | Biedermann ...... A61B 17/8057 606/323 |
| 2016/0157903 | A1 | * | 6/2016 | Choinski ............ A61B 17/8057 606/295 |
| 2018/0078299 | A1 | * | 3/2018 | Rossney ................ A61B 17/72 |

FOREIGN PATENT DOCUMENTS

| | | |
|---|---|---|
| EP | 2258290 A1 | 12/2010 |
| FR | 2483214 A1 | 12/1981 |
| WO | 8604798 A1 | 8/1986 |
| WO | 2007124099 A2 | 11/2007 |

OTHER PUBLICATIONS

Search Report dated Sep. 7, 2016 of corresponding International application No. PCT/IT2016/000074; 10 pgs.

* cited by examiner

INTRAMEDULLARY NAIL FOR THE TREATMENT OF FRACTURES OF THE LONG BONES

FIELD

The present invention relates to an intramedullary nail for the treatment of long bone fractures.

More precisely, the present invention relates to a pertrochanteric nail for the treatment of femur fractures.

BACKGROUND

In the cases of femur fractures, often it is resorted to the use of pertrochanteric nails for the treatment of the fracture. In several years a great variety of nails with even minimal differences between them have been realized, which able to put the surgeon in the conditions of treating the fracture. Each nail is normally coupled to one dedicated instruments.

In most cases, the installation provides for access from the proximal part of the femur for its insertion in the medullary canal. One or two locking devices are normally present in the proximal part of the nail while other locking devices are also present in the distal part.

The locking devices in the proximal area are normally one or two cephalic screws, with a thread suitable to grip in the cancellous bone present within the humeral head. Said screws are frequently blocked with appropriate systems placed by the nail head. This block positively prevents the screw from rotating and then modifying the mounting performed by the surgeon.

In case of using a single cephalic screw, even if blocked as said before, a great stability of the fragment of the femoral head is not obtained, as it is subject to rotational forces which are not counteracted by the screw itself.

Obviously, the situation improves in the case of use of two screws, or analogous systems, since the two devices normally act on two different, coplanar or non-coplanar, axes. In these conditions, the devices themselves will oppose to the force of rotation to which the head of the femur is subjected.

In any case, the grip in the cancellous bone of the femoral head is entrusted to the thread of said systems.

The invention of the present application refers to a pertrochanteric nail wherein there two fixing elements are provided, in the proximal part of the nail, inserted in the cancellous bone of the femoral head.

A similar nail is described for the proximal humerus in European patent EP 2258290 B1. In the Spanish patent ES 8 225 188 an application wherein two elements of proximal locking are provided is described, which are inclined so as to form with the nail axis a triangle, similarly to the present invention, but with the elements overlapping each other.

In European patent EP 2258290 B1 for humeral nail there is a similar arrangement with the fastening elements consisting of several screws for the grip in the bone and a stabilization screw of the blade-shaped element.

Said stabilization screw intersects the blade-shaped element and is inserted in a suitable hole, and then stabilizes the blade-shaped element, remaining free to move in any case on its own axis.

In such prior art devices, once implanted, it is barely possible to adjust the grip on the fracture, in order to adjust the correct insertion of the nail.

SUMMARY OF THE DISCLOSURE

Therefore, object of the present invention is to overcome the prior art problems, by means of an intramedullary nail that, once implanted, can be adjusted in such a way as to improve the alignment of the fracture fragment, and therefore the grip of the nail.

It is subject-matter of the present invention an intramedullary nail for the treatment of long bones fractures, in particular a pertrochanteric nail for the treatment of fractures of the femur, said nail having a body with a proximal area and a distal area and a longitudinal axis, said body of said nail being adapted to be inserted in the medullary canal of said long bone, said nail having at least two through holes formed at the proximal zone of said body, said nail comprising a pair of fastening elements each having a first and a second end, each fastening elements being adapted to be housed in a respective bore of the body of said nail in correspondence of the respective first end, said second ends of said fastening elements being adapted to engage with the cancellous bone of the long bone head in correspondence of the fracture to be treated, said fastening elements being configured so as to be fastenable to each other in the vicinity of the respective second end in a constraint configuration and, once constrained, so as to be movable independently of each other, in such a way that, during use, by acting on the respective first end of one or each fixing element, it is possible to act on the long bone head, moving it in a direction that is substantially parallel and/or transverse to the nail axis to achieve a reduction of the fracture fissure both bringing closer the fragment of the fracture and allowing its vertical realignment.

Furthermore, according to the invention, said first fastening element may present an intermediate portion between said first and second ends, and said second fixing element can presents an opening adapted to receive said intermediate portion of said first fastening element, said opening having such a size that, when said fastening elements are bound to each other in said constraint configuration, the passage of said first end of said first fastening element by the translation of said first fastening element in the absence of rotation is prevented, and to allow the release between said fastening elements from said constraint configuration, only by at least one rotation of said first fastening element relative to said second fastening element.

Always according to the invention, said intermediate portion of said first fastening element may presents a thickness smaller than the respective second end and may have a thickness smaller than said opening of said second fastening element, to be able to move freely with respect to said opening even in said constraint configuration.

Still according to the invention, said second fastening element may present the second end in the shape of a two tines fork and between said two tines there can be a cove-shaped slot comprising an inner opening portion and an outer opening portion, said outer opening portion being arranged in correspondence of the points of said two tines, said intermediate portion of said first fastening element having a cross section with a first side dimension larger than a second side dimension, transverse to the first, said inner opening portion of said second fork-shaped end having an slot between said two tines such as to enable accommodation of said intermediate portion of said first fastening element both with the larger side dimension and the smaller side dimension arranged transversely between said two tines, and said outer opening portion having a width between said two tines such as to enable accommodation of said intermediate portion of said first fastening element only with the smaller side dimension arranged transversely between said two tines, said nail being configured so that, during use, it constrains said fastening elements in said constraint configuration and it prevents the passage of said first end of said first fastening element through said opening of said second fastening element, when the larger side dimension of said intermediate portion is arranged transversely between said two tines of said second fastening element, and it allows the release of said fastening elements from said constraint configuration by means of the rotation of said first fastening element until the smaller side dimension of said intermediate portion is arranged transversely between said two tines of said second fastening element.

In particular, according to the invention, said intermediate portion of said first fastening element may present a quadrangular cross-section having two opposing major faces and two opposing minor faces.

Alternatively, according to the invention, said second fixing element can present a through hole adapted to receive said intermediate portion of said first fastening element in said constraint configuration, said through hole being shaped so that, during use, it permits the passage of said first end of said first fastening element by turning said first fastening element with respect to said second fastening element, and in said constraint configuration it prevents the passage of said first end of said first fastening element by moving said first fastening element with respect to said hole of said second fastening element, in the absence of rotation.

More in particular, according to the invention, said second end of said first fastening element may preferably be threaded in the form of large helix, in order, during use, to be bound, by rotation, to said cancellous bone of the long bone head in a constraint point.

Preferably, according to the invention, said hole of said second fastening element can present a plurality of notches such as to allow the passage of said first threaded end of said first fastening element by rotation, and to prevent in said constraint configuration the passage of said first end of said first fastening element by moving said first fastening element with respect to said hole of said second fastening element, in the absence of rotation, said threaded end going in abutment with said notches of said hole.

Furthermore according to the invention, said second end of said second fixing element can be point-shaped in such a way that, during use, it fits in the cancellous bone of the femoral head.

Furthermore, according to the invention, said second fixing element can present a curved shape, adapted to facilitate the coupling between said fixing elements.

Still according to the invention, said nail may include a control system for each fixing element, each coupled to the first end of a respective fastening element at said holes formed in the body of said nail, each of said control systems being adapted to be acting on said first end in order to cause, in said constraint configuration, the translation movement of each fixing element along its axis, without causing the rotation, so as to bring together and align the parts or fragments of the long bone fracture.

Always according to the invention, said nail body can present a different section between the proximal and the distal area.

Preferably according to the invention, the body can be drilled along its axis for at least a portion of its length, and can be closed in correspondence of at least its distal end.

In particular, according to the invention, said nail can comprise a cap adapted to be fixed to the distal end of said body for the bone cement blocking within the medullary canal, said cap being preferably of resorbable material.

Furthermore, according to the invention, said nail may include a plurality of openings, in particular holes or slots, in the distal part of said body, adapted to accommodate rotation locking elements and/or to allow bone cement outlet.

Finally, according to the invention, one or each of said fastening elements can provide a plurality of openings so that, once the implantation is realized, it is possible to inject bone cement to get it out from the openings provided in the distal part of the nail body.

BRIEF DESCRIPTION OF THE DRAWING

The invention will be now described, by way of illustration but not by way of limitation, with particular reference to the figures of the accompanying drawings, in which.

DETAILED DESCRIPTION OF THE DRAWING

Figure 1:
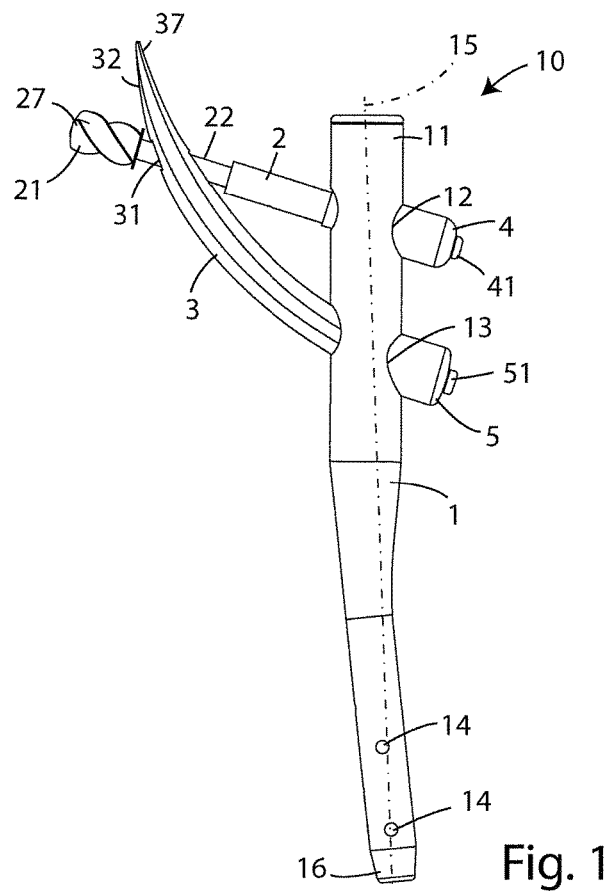
FIG. 1 shows a side view of the intramedullary nail according to the invention in a first embodiment.
Figure 2:
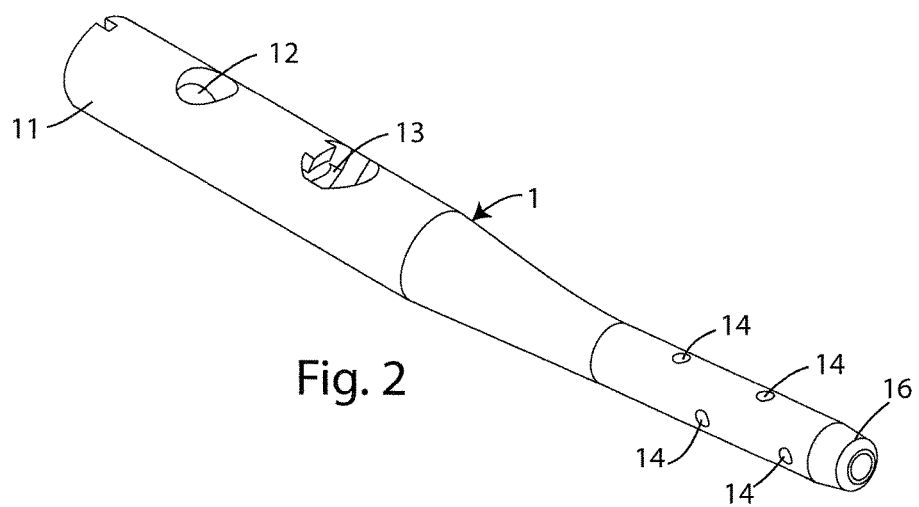
FIG. 2 shows a perspective view of the intramedullary nail body of FIG. 1.
Figure 3:
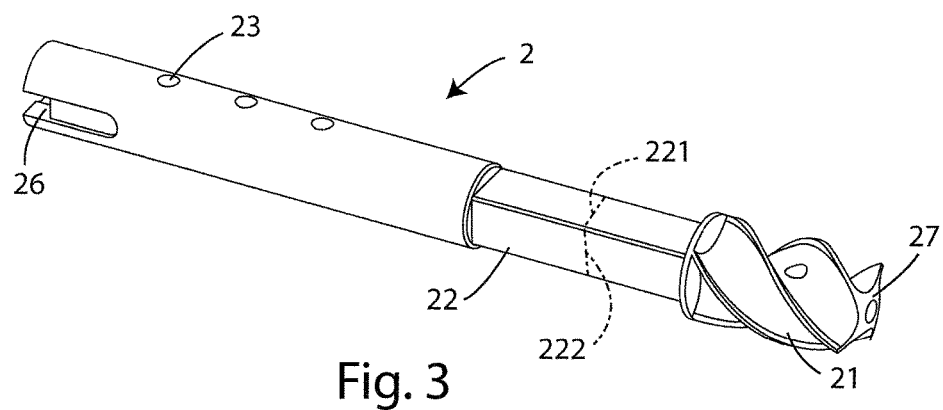
FIG. 3 shows a perspective view of the first fastening element or intramedullary nail fixing screw of FIG. 1.
Figure 4:
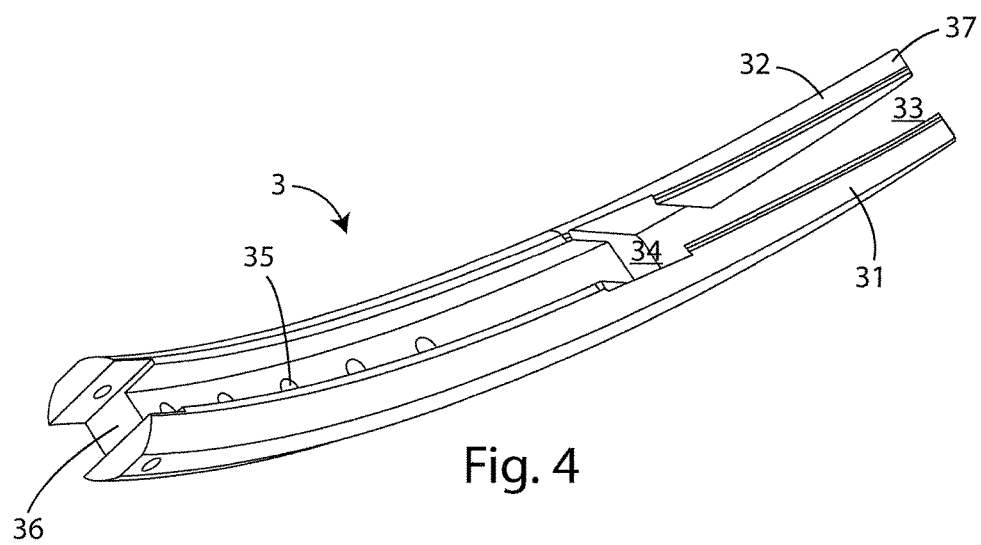
FIG. 4 shows a perspective view of the second fastening element or tip-blade of the intramedullary nail of FIG. 1.
Figure 5:
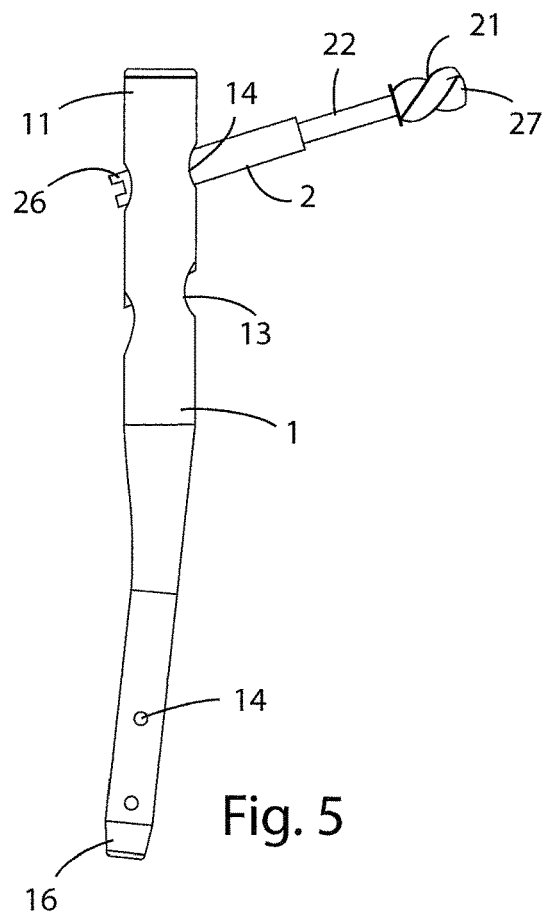
FIG. 5 shows a side view of the intramedullary nail of FIG. 1 in a first stage of assembling of the fixing screw of FIG. 3.
Figure 6:
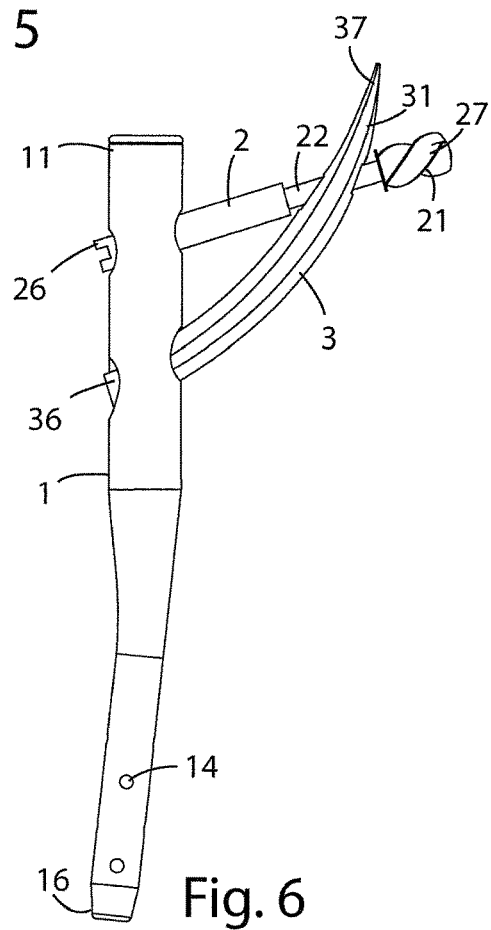
FIG. 6 shows a side view of the intramedullary nail of FIG. 1 in a second step of assembling of the tip-blade of FIG. 4.
Figure 7:
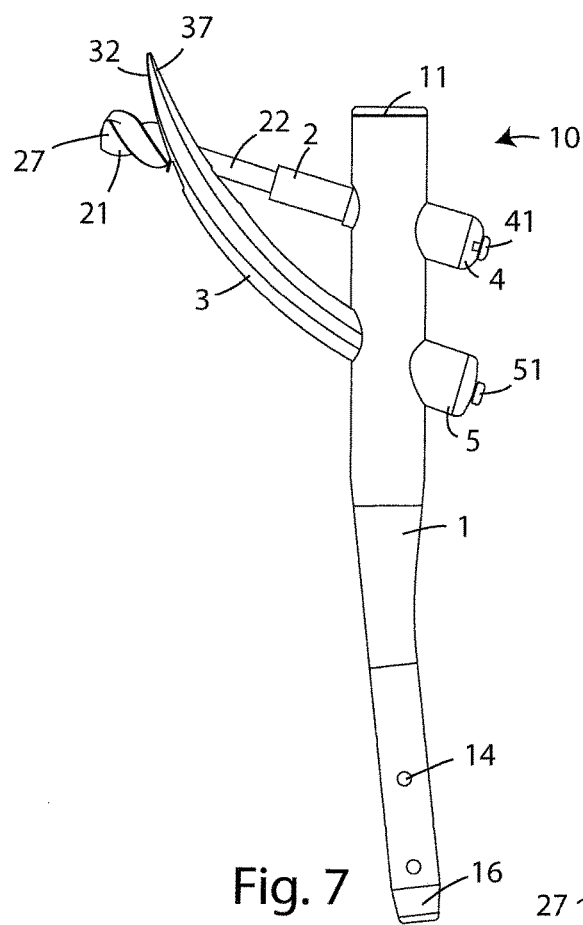
FIG. 7 shows a side view of the intramedullary nail of FIG. 1 in a different configuration relative to the mutual interaction of the two fixing elements.
Figure 8:
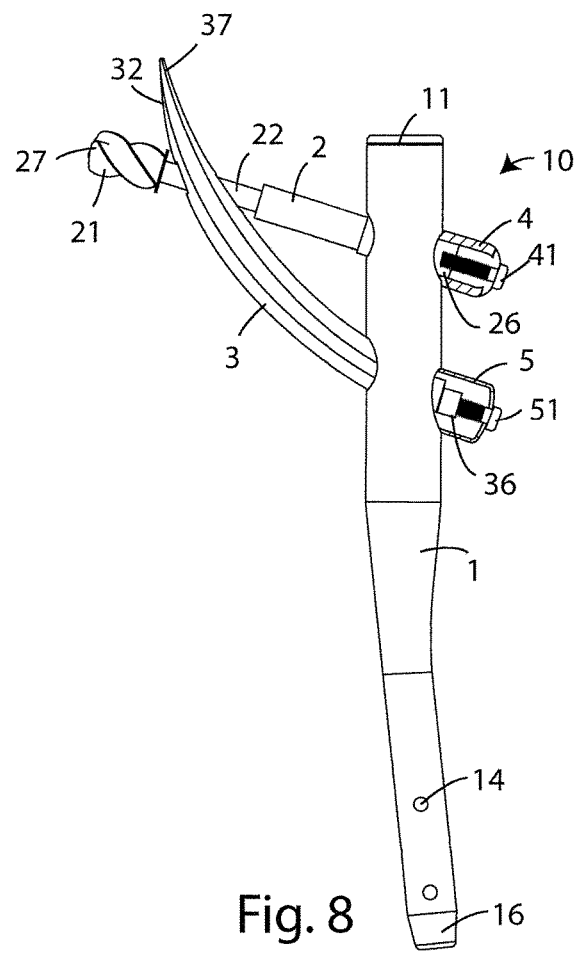
FIG. 8 shows a side view of the intramedullary nail of FIG. 1 in which one can see the retraction systems of the two fixing elements.
Figure 9:
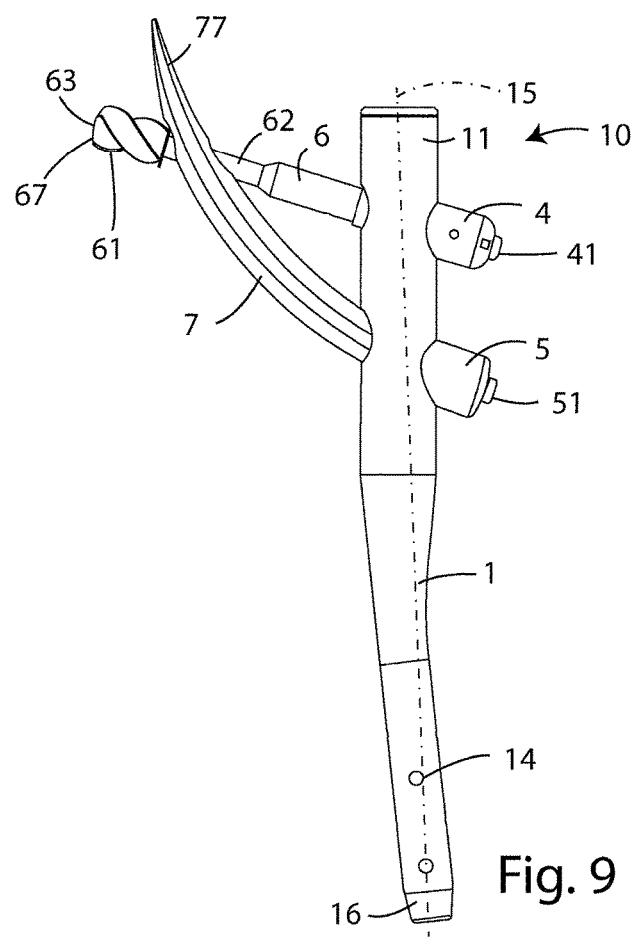
FIG. 9 shows a side view of the intramedullary nail according to the invention in a second embodiment.
Figure 10:
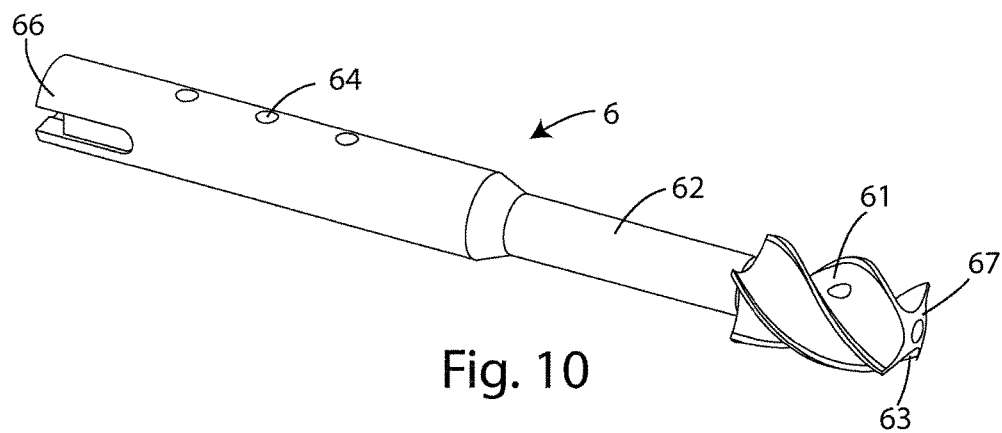
FIG. 10 shows a perspective view of the first fastening element or intramedullary nail fixing screw of FIG. 9.
Figure 11:
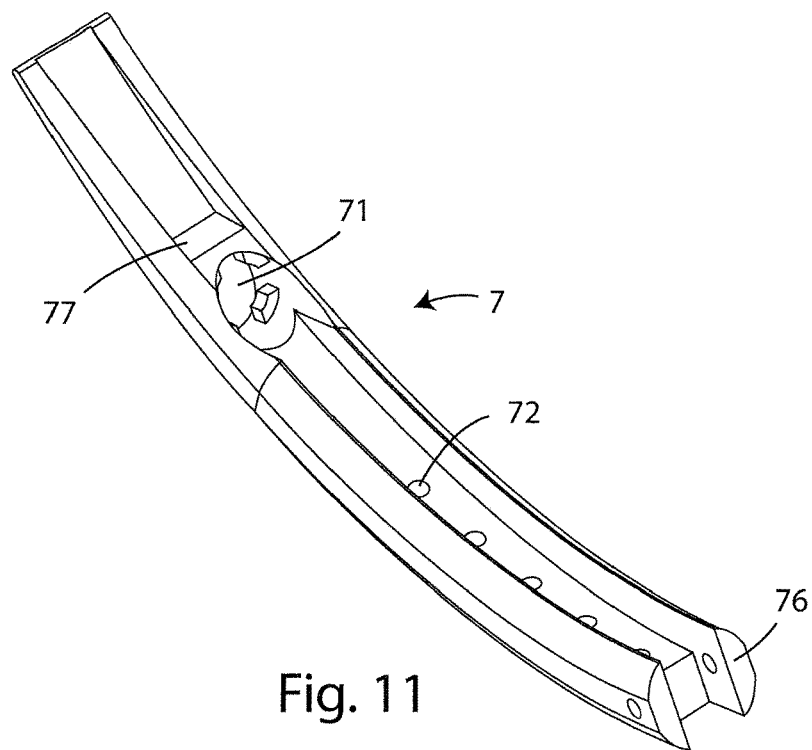
FIG. 11 shows a perspective view of the second fastening element or tip-blade of the intramedullary nail of FIG. 9.
Figure 12:
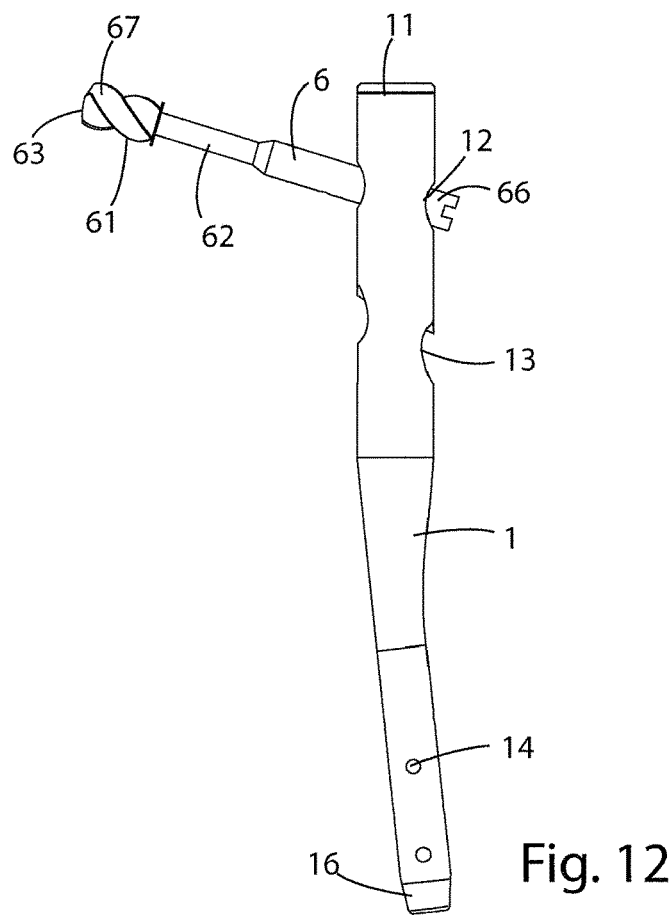
FIG. 12 shows a side view of the intramedullary nail of FIG. 9 in a first stage of assembling of the fixing screw of FIG. 10.
Figure 13:
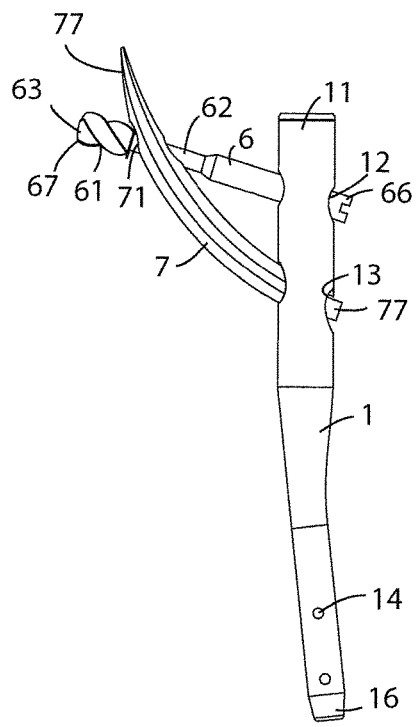
FIG. 13 shows a side view of the intramedullary nail of FIG. 9 in a second assembling phase of the tip-blade of FIG. 11.
Figure 14:
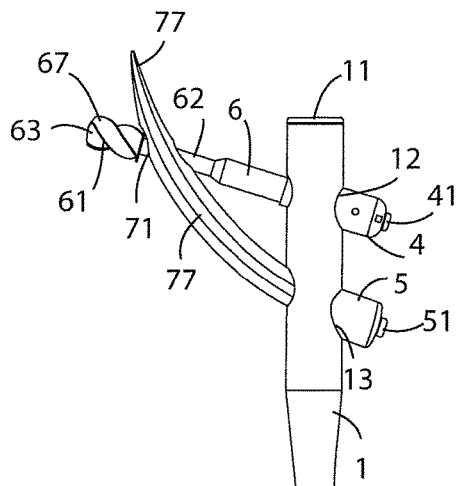
FIG. 14 shows a side view of the intramedullary nail of FIG. 9 in a different configuration relative to the reciprocal interaction of the two fixing elements.
Figure 15:
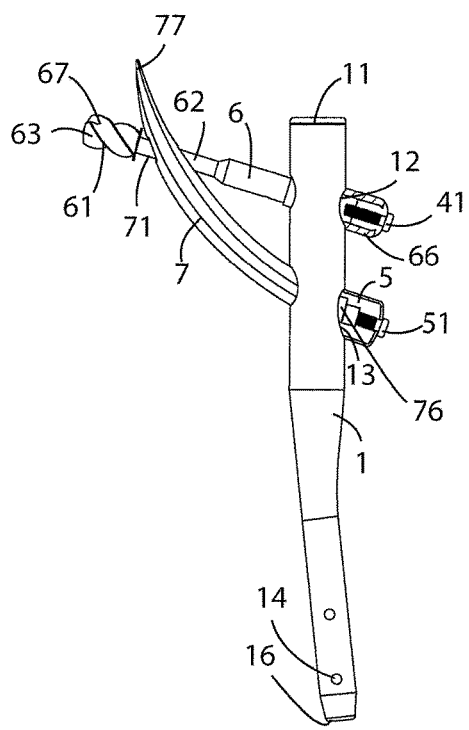
FIG. 15 shows a side view of the intramedullary nail of FIG. 9 in which one can see the retraction systems of the two fixing elements.

Referring to FIGS. 1-8, there is a first embodiment of the intramedullary nail according to the invention indicated by the reference number 10.

Said intramedullary nail 10 has been developed for the treatment of femoral fractures, dealing specifically with a pertrochanteric nail. However, the same nail may be employed, with the necessary dimensional changes, for the treatment of fractures of long bones, for example for humerus fractures. As it is known, the long bones, including the femur and humerus, have a relatively long body, or diaphysis, and two expanded ends, or epiphyses. The diaphysis is a tubular structure comprising a medullary canal, disposed in the central part of the bone cavity, surrounded by the cancellous bone and by an outer layer of compact bone. The upper epiphysis, in correspondence of the articulation constraint, is termed long bone head and contains the cancellous bone surrounded by a thin layer of cortical bone or compact bone, not containing bone marrow.

The intramedullary nail 10 according to the invention has a body 1 having a proximal area or portion 11 and a distal zone or portion 16 and a longitudinal axis 15. Preferably, the body 1 of the nail 10 has a different cross section between the proximal zone 11 and the distal zone 16, in particular, the distal area 16 is less thick than proximal area 11, and this allows avoiding having to bore with a greater diameter the entire cavity of the femur for the housing of the nail. The body 1 of the nail 10 is adapted to be inserted in the medullary canal of the femur, at the head of the femur, as shown in FIGS. 1 and 18a-18c.

According to the first embodiment, as mentioned given by way of illustration but not by way of limitation, in the proximal part 11 of the body 1 of the nail 10 there are two through openings or holes 12 and 13 through which two fixing elements 2 and 3 are made passing.

The first fastening element 2, preferably a fastening element in the form of screw 2, in particular a cephalic screw, has a first 26 and a second 27 ends. The second end 27 is adapted to engage the cancellous bone of the long bone head in correspondence of the fracture to be treated. In particular, in said second end or part of the tip 27 has a thread 21 suitable to grip, by rotation, the cancellous bone of the femoral head in a constraint point, such a thread 21 being preferably a large helix. In the specific embodiment, the section of this screw 2, in the rear area 22 of the threaded part 21, or intermediate portion 22 between the two ends 26 and 27, is shaped such as to have a side 222 having length smaller than the length of the other side 221. In any case such an intermediate portion 22 is of lesser thickness with respect to at least the first end 26, if not even smaller than the second end 27. In the specific embodiment, the section of said intermediate portion 22 is rectangular, with two opposite sides 222 having length smaller than the other two opposite sides 221. However, in other embodiments, the section of said intermediate portion 22 can also be of other shapes, for example elliptical, provided that it presents a first side dimension larger than a second side dimension, transverse to the first. Therefore, in the case of ellipse, a major axis having length larger than the minor axis.

The first end 26 of the first fastening element 2 has a shape such as to allow a tool 8 specifically designed to act on it to cause the rotation of the screw body 2.

Figure 16:
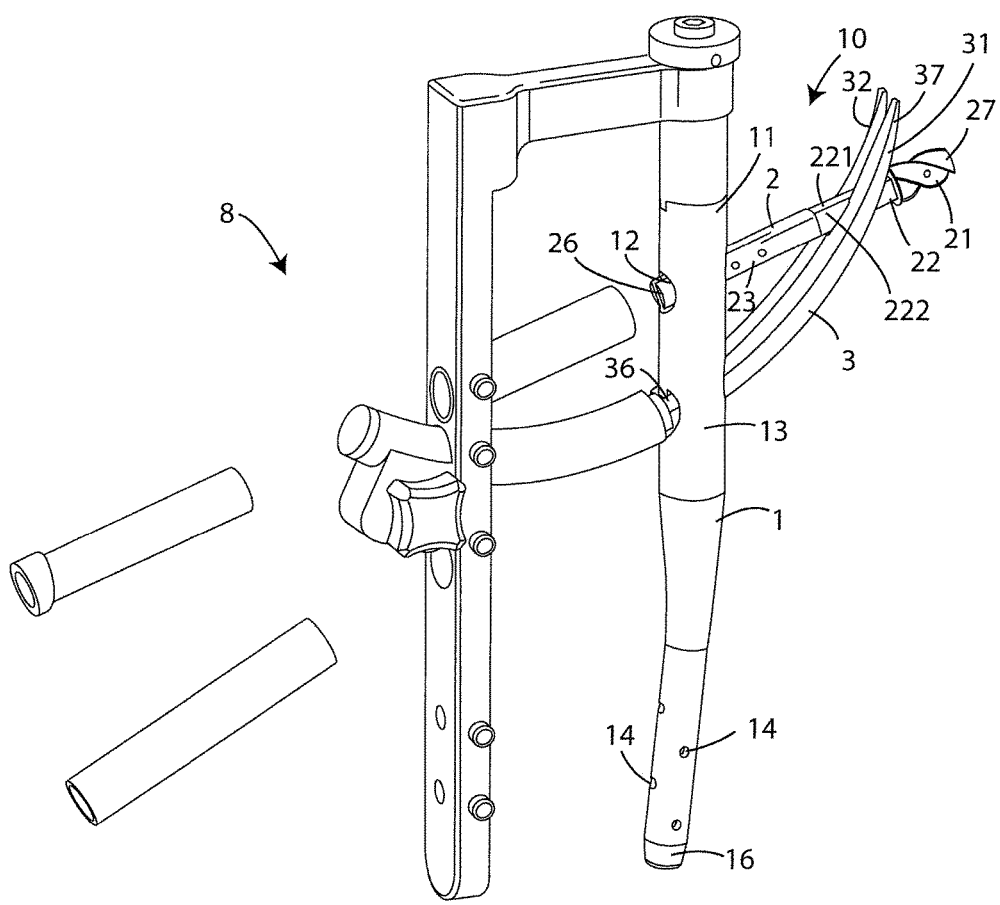
FIG. 16 shows an exploded perspective view of the instrumentation for the implantation of the intramedullary nail of FIG. 1.

Making use of the specific instrument 8, shown in FIG. 16, it is possible to insert such a screw 2 into the opening 12 in the body 1 of the nail 10 and screw it in the femoral head by acting on the first end 26, stopping it in a position such that the faces comprising the major sides 221 of the section of the intermediate portion 22 of said screw 2 are on a plane substantially parallel to a plane comprising the axis 15 of the body 1 of the nail 10 and such that the screw 2 presents the first end 26 substantially disposed in said opening 12 of the body 1 of the nail 10.

Also the second fastening element 3 has a first 36 and a second 37 ends. In the present embodiment, the second end 37 presents a fork-shape with two tines 31 and 32 and preferably the body of the second fastening element 3 is curved, in order to facilitate the coupling with the first fastening element 2. Between the two tines 31 and 32, a cove-shaped opening 33, 34 with variable section is arranged, in other words the width of the slot between the tines 31 and 32 of the fork has two sections 33 and 34. The outer section 33, at the apex of the tines 31 and 32, has a width smaller than the width of the inner section 34 of the cove-shaped opening. The inner section 34 has a width such as to allow the passage/receipt of the intermediate portion 22 of the screw 2, both if they are oriented with the face comprising either the minor side 222 or the longer side 221, the face being arranged on a plane parallel to a plane containing the axis 15 of the body 1 of the nail 10. Instead, the outer section 33 has a width such as to allow the passage/receipt of the intermediate portion 22 of the screw 2, only if oriented with the face comprising the major side 221 on a plane parallel to the plane containing the axis 15 of the body 1 of the nail 10. Preferably, this inner section 34 is an opening of rectangular section having a cross-section slightly larger than the section of the intermediate portion 22 of the screw 2, and is contiguous with the outer section 33, which is an opening of constant width slightly greater than the length of the face comprising the lower side 222 of the section of the intermediate portion 22 of the screw 2.

Always making use of instruments 8 of FIG. 16, it is possible to insert the second fixing element 3 in the second opening 13 formed in the body 1 of the nail 10. The external section 33 in the tip 37 of said second fastening element 3 is such that it can be inserted into cancellous bone of head of the femur until crossing and going beyond the screw 2 which at this time is oriented so that the face comprising the lower side 222 of the section of the intermediate portion 22 of the screw 2 passes through the inner 34 and outer 33 sections of the opening of the fork-shaped end 37 of the tip-blade 3. Proceeding with the inclusion of this fork-shaped element 37 of the tip-blade 2, the intersection between the two fastening elements 2 and 3 is made moving into fork part 37 with greater diameter 34.

After reaching this position 34, it is possible to act again on the first end 26 of the screw 2 causing the rotation of the screw 2 so that the faces comprising the major sides of the section 221 of the intermediate portion 22 of the screw 2 are on a plan orthogonal or transversal, or in any case not parallel, to the plane containing the axis 15 of the body 1 of the nail 10. In the this position, the two fastening elements 2 and 3 are mutually bound, as well as bound to the femoral head, in a constraint configuration, not being possible to further retract the screw 2 in that the threaded part 21 is larger than the width of the inner section 34 of the fork 37 of the tip-blade 3 and not even being possible to retract the blade-shaped tip 3, being the width of the face comprising the major side 221 of the section of the intermediate portion, in other words of the rectangle 221 orthogonal to the axis of the tip-blade, larger than the width between the tines 31 and 32 in the first part or outer section 33 of the fork 37 of the tip-blade 3.

The intramedullary nail 10 according to the invention may also comprise suitable devices or retraction or adjustment systems 4, 5 coupled to the first ends 26 and 36 of the fastening elements 2 and 3 which are in the openings 12 and 13 of the body 1 of the nail 10, which allow the translatory motion, and thus the retraction, of the two fixing elements 2 and 3 along the respective longitudinal axes, without their rotation, so that it is possible to reduce the fracture, both in the sense of compaction and in the sense of vertical re-aligning of the fracture fragment.

Figure 17A:
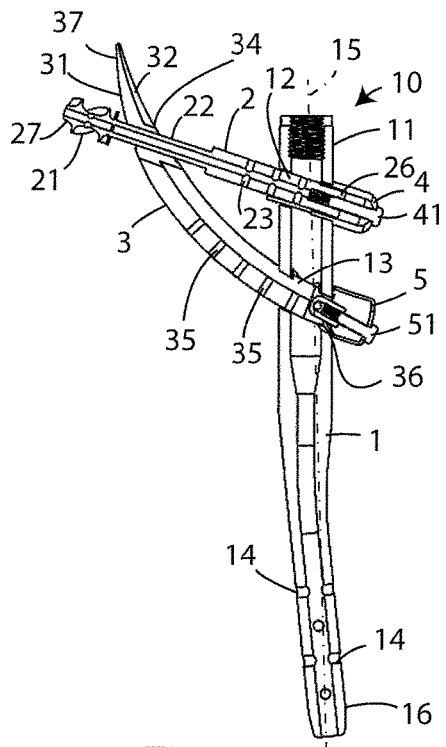
FIGS. 17a-17c show three side cross-section views of the intramedullary nail of FIG. 1 in three different configuration of adjustment of the fastening elements.
Figure 17B:
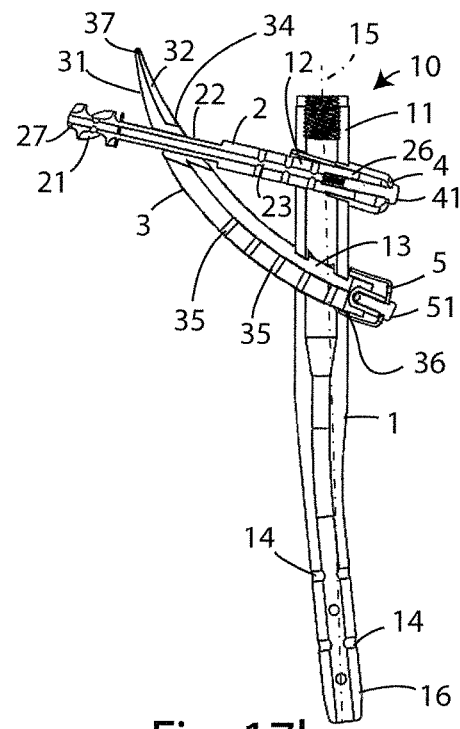
Figure 17C:
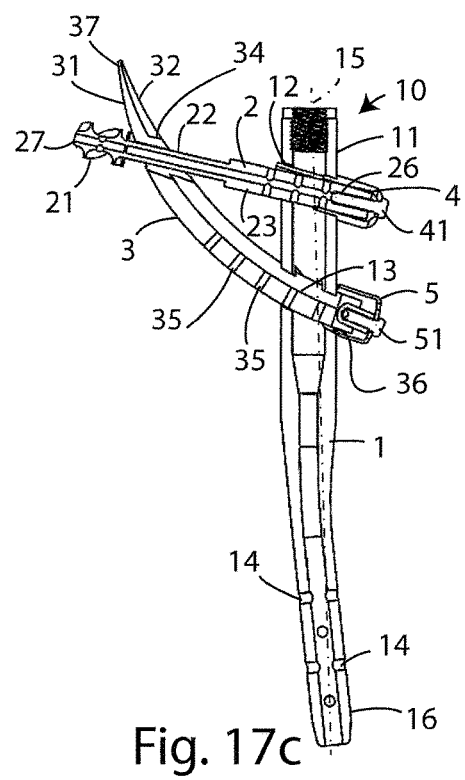

Said retraction systems 4 and 5 provide adjusting elements 41 and 51, in particular a screw, able to engage with the respective first ends 26 and 36 of the fastening elements 2 and 3 and to push or retract them as shown in FIGS. 17a-17c.

In particular, said FIG. 17a shows a first adjustment configuration, in which the fastening elements 2 and 3, in said constraint configuration, are in a condition of substantially maximum extraction.

In FIG. 17b, the adjustment element 51, i.e. a screw, acting on the second fastening element 3, after being screwed into the respective seat in correspondence of the first end 36, has caused the almost complete retraction of said second fastening element 3, making it move on its own axis. In this position, the inner section 34 of the cove-shaped opening of the second fastening element 3 having acted on the intermediate portion 22 of the first fastening element 2 has caused the variation of its inclination angle, substantially lowering the second end 27.

In FIG. 17c also the adjustment element 41, also a screw, acting on the first end 26 of the first fastening element 2, after having been screwed in the respective seat, has retracted almost completely said first fastening element 2, making it move on its own axis, and then approaching its second end 27 to opening 33, 34 of said second fastening element 3.

Therefore, it can be summarized that the translation of the second fastening element 3 on its own axis, by acting by means of the opening 33, 34 on the intermediate portion 22 of the second fixing element 2, in addition to varying the point in which it engages with the cancellous bone of the femoral head, causes the variation of the inclination of the first fastening element 2, lowering and raising its second end 27, causing the vertical, or substantially parallel to the axis 15 of the nail 10, displacement of the point of anchor/engagement or constraint to cancellous bone of the femoral head. The translation of the first fastening element 2 on its own axis, always taking place inside the opening 33, 34 of the second fastening element 3 causes the displacement of the point of anchor/engagement or constraint of its second end 27 to the cancellous bone on a coplanar, substantially horizontal plane. Therefore, the combination of the two movements allows correcting and realigning the fracture, as illustrated in the following.

In fact, the combination or interaction of the bound two mounting elements 2 and 3 makes it possible, through their bond and the possibility of retract them independently via the adjustments 41, 51 present, to compact and realign the fracture by means of independent translation of the fastening elements 2 and 3. By allowing the movement of the femoral head both in the direction of the nail 10 and in the vertical direction, it allows therefore to raise or lower the fragment, realigning it.

Figure 18A:
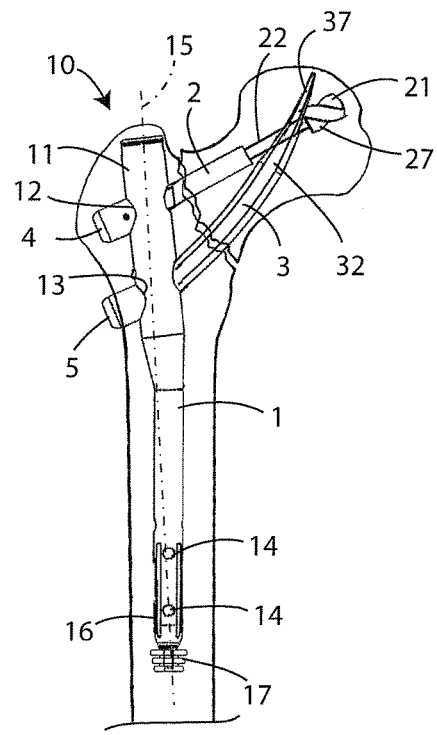
FIGS. 18a-18c show three side views of the intramedullary nail of FIG. 1 in three different further configurations of adjustment of the fixing elements.
Figure 18B:
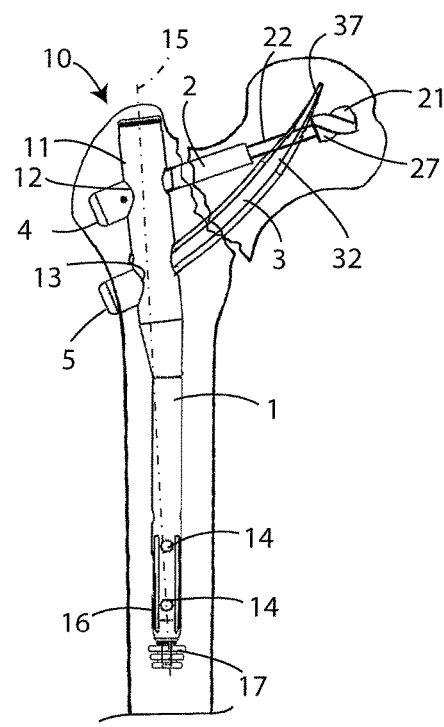
Figure 18C:
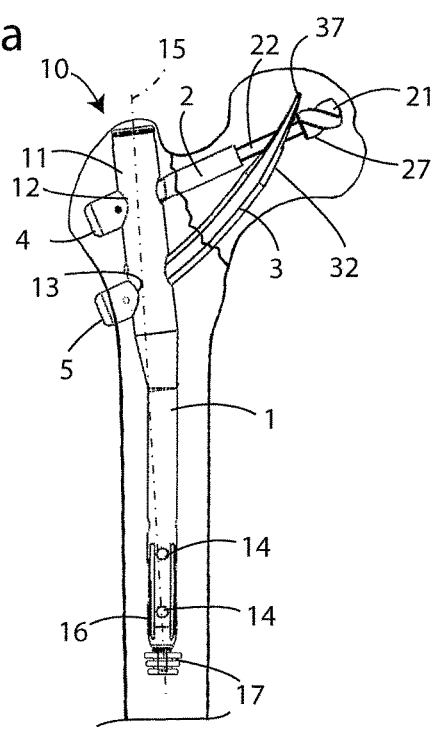

An example of such movement is visible from FIGS. 18a-18c, in which the intramedullary nail 10 according to the invention is inserted at the head of the femur. As can be observed, in order to allow a correct realignment of the fragment of the fracture, by adjusting the offset of the fastening elements 2, 3 about their axes, it is possible to act on the point of constraint of the second end 27 of the first fastening element 2, and then on the fragment of the fracture until obtaining the correct alignment, lifting the point of constraint to a second end 27 of the first fastening element 2 to cancellous bone (as shown in FIG. 18a) or lowering (as shown in FIG. 18b) or disposing it in a more centered position (as shown in FIG. 18c).

This therefore allows correcting and adjusting the point of engagement and anchoring of the nail once it has been inserted into the femoral head, without incurring an invasive intervention following the insertion of the nail.

With said invention, a surgery can therefore advantageously be performed, which is able to realize a perfect fracture reduction according to different axes, reducing the complications. The load is distributed on the two fastening elements and not only on a cephalic screw, preventing rotation of the femoral head.

The nail 10 and the two fastening elements 2 and 3 are preferably designed so that, after implantation as described above, it is possible to insert, on the proximal part of the femur, the bone cement which, through suitable openings, reaches the distal part of the devices.

Figure 19:
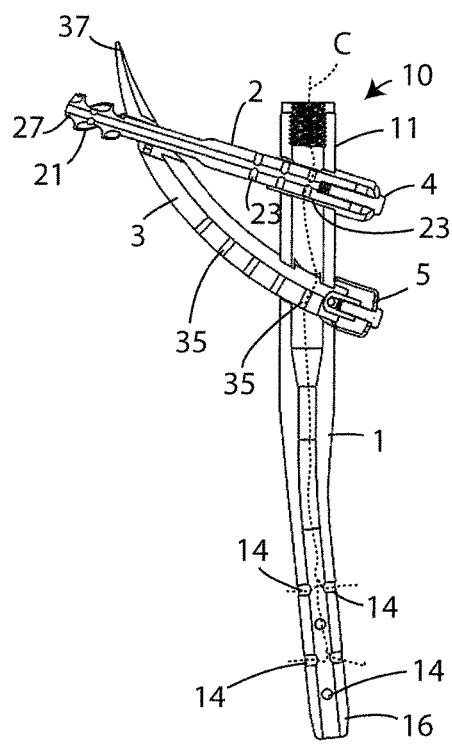
FIG. 19 shows a side section view of the intramedullary nail of FIG. 1 during the process of insertion of the bone cement.
Figure 20:
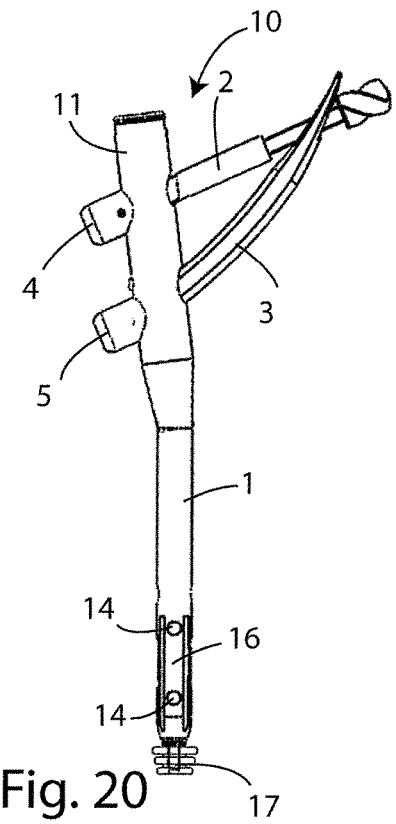
FIG. 20 shows a side view of the intramedullary nail of FIG. 1 with the cap inserted into the distal end for the blocking of the bone cement.

In particular, as shown in FIG. 19, the body 1 of the nail 10 may be drilled along its axis 15 from the proximal end 11 for almost its entire length for passage of bone cement C to be inserted once the operation of insertion of the nail 10 and the correction of the fastening elements 2 and 3 are completed, to fix in position the nail in the femur 10. As shown in FIG. 20, a cap 17 may be provided, which is adapted to be fixed to the distal end 16 of said body 1 for blocking the bone cement within the medullary canal, said cap 17 being preferably of resorbable material.

Appropriate and any openings in the distal portion may allow the insertion of screws for the distal locking of the nail.

Figure 21:
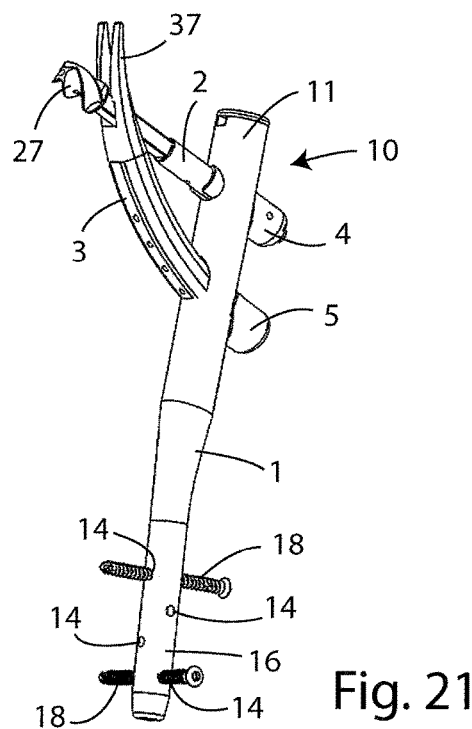
FIG. 21 shows a perspective view of the intramedullary nail of FIG. 1 comprising additional fixing elements at the distal portion.

As shown in FIG. 21, the body 1 of the nail 10 may include a plurality of openings 14, in particular holes or slots, in the distal part 16 of the body 1, adapted both to house more fastening elements 18 for blocking the rotation of the nail 10 and/or for allowing the removal of the bone cement C previously inserted (as shown in FIG. 19).

Each or even only one of said fastening elements 2, 3 can provide a plurality of respective openings 23; 35 so that, once the implant is executed, it is possible to inject the bone cement to get it out from the openings 14 arranged in the distal part 16 of the body 1 of the nail 10 (as shown in FIG. 19).

In FIGS. 9-15, it is observed a second embodiment of the intramedullary system according to the invention always indicated by the reference number 10.

In this case the two fastening elements are formed by a first fixing element 6, in particular a screw 6 completely similar to the previous case, but of circular cross-section, particularly in correspondence of the intermediate portion 62, and by a second fixing element 7, in particular a tip-blade 7, preferably curved, with special hole 71 for the interaction with the screw 6, in particular said hole 71 is made in such a way that the threaded portion 61 of the screw 6 can pass only by turning the screw 6 itself. This hole 71 is of a diameter such that the core 63 of the threaded part 61 of the screw 6 and the shank part 62 that follows the threaded portion 61 can pass through. The pitch of the thread 61 is such that it can pass through the hole 71 of the tip-blade 7. Once the threaded portion 61 has passed the tip-blade 7, the two elements 6 and 7 are bound as in the previous case. The rest of the operation remains the same.

In fact, in this embodiment, instead of presenting, in correspondence of the second end 77, a cove-shaped opening, there is a hole 71 having notches which permit the passage by rotation of the thread 61 of the first fastening element, but prevent the translation, since the threaded portion 61 of the first fixing element 6, once passed through the hole 71 by rotation, should be in abutment with the notches of said hole 71 when it is translated on its own axis, without rotation.

The nail 10, according to the second embodiment, is implanted using a special instrument and involves first the insertion of the body 1 of the nail in the medullary canal, the subsequent insertion of the second fixing element 7 in the respective opening 13 formed in the body 1 of the nail 10 until the second tip-shaped end 77 engages the cancellous bone of the femoral head, followed by insertion of the first fastening element 6 by means of the respective opening 12 in the body 1 of the nail 10 by acting on its first end 66, causing the rotation of said first fastening element 6 in such a way as to allow the passage of the threaded portion 61 through the hole 71 in the second fastening element 7, until the threaded portion 61 is not engaged with the cancellous bone of the femoral head in a point of constraint and the threaded part 71 is not completely passed behind said hole 71. At that point, the two fastening elements 6 and 7 are bound to each other, as well as bound to the femoral head, in a constraint configuration, and, acting on the respective first ends 66 and 76, for example by means of the respective means of retraction 4 and 5, it is possible to translate each element independently without that the two elements can disengage from each other and realizing a reduction of the fracture both bringing closer the fragment the fracture and allowing its vertical realignment.

Therefore, as described above, it is sufficient that the intramedullary nail according to the invention, independently from the described embodiments, presents said fastening elements configured to be fastened to each other in the vicinity of the respective second end in a configuration of constraint and, once bound, to be movable independently of each other, in such a way that, during use, by acting on the respective first ends of one or each fastening element, it is possible to act on the long bone head, moving the latter in substantially parallel direction and/or a direction transverse to the axis of the nail, to achieve a reduction of the fracture fissure both bringing closer the fragment of the fracture and allowing its vertical realignment. Indeed, since the two fastening elements are constrained to each other, by translating a fastening element along its axis, one acts also on the second fastening element, which in turn acts on the fracture fragment on which it is engaged.

In addition, more particularly, the intramedullary nail according to the invention, for each of the illustrated embodiments, is configured in such a way that the opening of the second fastening element is arranged to receive said intermediate portion of said first fastening element and is of such size, when said fastening elements are bound to each other in said constraint configuration, to prevent the passage of said first end of said first fastening element by the translation of said first fastening element in the absence of rotation, and to allow the release between said fastening elements from said constraint configuration, only by at least one rotation of said first fastening element relative to said second fastening element. This allows to individually adjusting each fastening element by translation, causing the displacement, and therefore the correction, of the fragment of the fracture, realigning it.

In the foregoing, preferred embodiments have been described and variants of the present invention have been suggested, but it is to be understood that those skilled in the art can make modifications and changes, without so departing from the related scope of protection, as defined by the attached claims.

The invention claimed is:

1. An intramedullary nail for the treatment of fractures of long bones, in particular a pertrochanteric nail for the treatment of fractures of the femur, comprising:

a nail body with a proximal area and a distal zone and a longitudinal axis, said body of said nail being adapted to be inserted in the medullary canal of said long bone, said nail having at least two through holes formed in the proximal area of said body, said nail having a pair of fastening elements each having a first and a second end, each fastening element being adapted to be housed in a respective hole of the body of said nail at the respective first end, wherein said second ends of said fastening element are adapted to engage the cancellous bone of the long bone head at the fracture to be treated, said fastening elements being configured so that they can be bound to each other in the vicinity of the respective second end in a constraint configuration and, once bound, so as to be displaceable independently of one another, so that, during use, by acting on the respective first end of one or each fastening element, it is possible to act on the long bone head, moving it in a direction substantially parallel and transverse to the axis of the nail, to realize a reduction of the fracture fissure by both bringing closer the fragment of the fracture and allowing its vertical realignment, wherein said first fastening element has an intermediate portion between said first and second ends and in that said second fastening element has an opening adapted to receive said intermediate portion of said first fastening element, said opening having a size that, when said fastening elements are bound to each other in said constraint configuration, the passage of said first end of said first fastening element by the translation of said first fastening element in the absence of rotation is prevented, and to allow the release between said fastening elements from said constraint configuration, only by at least one rotation of said first fastening element relative to said second fastening element, wherein said intermediate portion of said first fastening element has a thickness smaller than the thickness of the respective second end and presents a smaller thickness than said opening of said second fastening element to be able to move freely with respect to said opening also in said constraint configuration.

2. The intramedullary nail according to claim 1, wherein said second fastening element has the second end in the form of a two-tines fork and between said two tines a cove-shaped opening is formed which includes an inner opening portion and an outer opening portion, said outer opening portion being arranged in correspondence of the points of said two tines, said intermediate portion of said first fastening element having a cross-section with a first side dimension larger than a second side dimension, transverse to the first, said portion of inner opening of said second fork-shaped end having a slot between the two tines such as to enable reception of said intermediate portion of said first fastening element both with the larger side dimension and the smaller side dimension which is disposed transversely between said two tines, and said outer opening portion having a width between said two tines such as to enable reception of said intermediate portion of said first fastening element only with the smaller side dimension disposed transversely between said two tines, said nail being configured in such a way to constrain, during use, said fastening elements in said constraint configuration and to prevent the passage of said first end of said first fastening element by said opening of said second fastening element, when the larger side dimension of said intermediate portion is arranged transversely between said two tines of said second fastening element, and to allow the release of said fastening elements from said constraint configuration by rotation of said first fastening element until the smaller side dimension of said intermediate portion is arranged transversely between said two tines of said second fastening element.

3. The intramedullary nail according to claim 1, wherein said intermediate portion of said first fastening element has a quadrangular cross-section having two larger faces opposite to one another and two opposite smaller faces.

4. The intramedullary nail according to claim 1, wherein said second fastening element has a through hole adapted to receive said intermediate portion of said first fastening element in said constraint configuration, said through hole being shaped in such a way that, during use, it permits the passage of said first end of said first fastening element by rotating said first fastening element with respect to said second fastening element, and it prevents, in said constraint configuration, the passage of said first end of said first fastening element displacing said first fastening element with respect to said hole of said second fastening element, in the absence of rotation.

5. The intramedullary nail according to claim 1, wherein said second end of said first fastening element is threaded, in the shape of a wide helix, in order, during use, to be bound, by rotation, to said cancellous bone of the head of the long bone in a constraint point.

6. The intramedullary nail according to claim 1, wherein said hole of said second fastening element presents a plurality of notches such as to allow the passage of said first threaded end of said first fastening element by rotation, and to prevent, in said constraint configuration, the passage of said first end of said first fastening element displacing said first fastening element with respect to said hole of said second fastening element, in the absence of rotation, said threaded end going in abutment with said notches of said hole.

7. The intramedullary nail according to claim 1, wherein said second end of said second fastening element is point-shaped in such a way that, during use, it inserts in the cancellous bone of the femoral head.

8. The intramedullary nail according to claim 1, wherein said second fastening element has a curved shape, adapted to facilitate the coupling between said fastening elements.

9. The intramedullary nail according to claim 1, further comprising:

an adjustment system for each fastening element, each coupled to the first end of a respective fastening element in correspondence with said holes formed in the body of said nail, each of said adjustment systems being adapted to being acting on said first ends in order to cause, in said constraint configuration, the translation movement of each fastening element along its axis, without causing the rotation, so that to bring closer and align the parts or fragments of the fracture of said long bone.

10. The intramedullary nail according to claim 1, wherein the body has a different section between the proximal zone and distal zone.

11. The intramedullary nail according to claim 1, wherein the body is bored along its axis for at least a portion of its length, and in that it is closed at least at its distal end.

12. The intramedullary nail according to claim 1, further comprising:

a cap adapted to be fixed to the distal end of said body for the bone cement blocking within the medullary canal, said cap being preferably in resorbable material.

13. The intramedullary nail according to claim 1, further comprising:

a plurality of openings, in particular holes or slots, in the distal part of said body, which are adapted to accommodate blocking elements for blocking the rotation and permitting the leakage of bone cement.

14. The intramedullary nail according to claim 1, wherein one or each of said fastening elements include a plurality of openings such that, once the implant is realized, it is possible to inject the bone cement to get it out from the openings pre-arranged in the distal part of the body of the nail.

* * * * *